United States Patent [19]

Columbus

[11] 4,136,036
[45] Jan. 23, 1979

[54] COLLECTION AND DISPENSING DEVICE FOR NON-PRESSURIZED LIQUIDS

[75] Inventor: Richard L. Columbus, Rochester, N.Y.

[73] Assignee: Eastman Kodak Company, Rochester, N.Y.

[21] Appl. No.: 879,930

[22] Filed: Feb. 22, 1978

Related U.S. Application Data

[63] Continuation-in-part of Ser. No. 674,462, Apr. 7, 1976, abandoned.

[51] Int. Cl.² .............................................. B01D 21/26
[52] U.S. Cl. ................................ 210/516; 128/2 F; 128/2 G; 128/DIG. 5; 210/540; 210/DIG. 23; 222/548; 233/1 R; 233/26
[58] Field of Search ................. 210/65, 78, 83, 360 R, 210/361, 460, 512 R, 513, 515, 516, 22 R, 321 B, 540, DIG. 23, DIG. 24; 235/92 R, 92 V, 92 PC; 128/2 F, 2 G, 213, 272, 276, DIG. 5; 261/DIG. 54; 23/258.5, 253 R; 233/1 R, 26; 222/522, 523, 553, 548; 73/425.4 P

[56] References Cited

U.S. PATENT DOCUMENTS

| 1,924,057 | 8/1933 | Draper et al. ................. 222/522 X |
| 2,369,577 | 2/1945 | Kielland ........................ 235/92 R X |
| 2,779,232 | 1/1957 | Small ............................ 235/92 PC |
| 2,807,416 | 9/1957 | Parker et al. ................. 235/92 PC |
| 2,851,066 | 9/1958 | Ott et al. ...................... 222/522 X |
| 2,875,666 | 3/1959 | Parker et al. ................. 235/92 V |
| 2,941,869 | 6/1960 | Brown et al. ................. 23/253 R |
| 3,433,216 | 3/1969 | Mattson ........................ 128/2 F |
| 3,513,829 | 5/1970 | Deuschle et al. ............ 128/276 X |
| 3,610,226 | 10/1971 | Albisser ...................... 128/2 F |
| 3,623,475 | 11/1971 | Sanz et al. .................. 128/DIG. 5 |
| 3,630,191 | 12/1971 | Gilford ......................... 210/DIG. 24 |
| 3,640,267 | 2/1972 | Hurtig et al. ............... 128/2 F |
| 3,645,252 | 2/1972 | Gilford ......................... 128/2 F |
| 3,703,800 | 11/1972 | Courbon ...................... 261/DIG. 54 |
| 3,741,732 | 6/1973 | Stanfield ..................... 73/425.4 P |
| 3,750,645 | 8/1973 | Bennett et al. .............. 210/78 X |
| 3,763,705 | 10/1973 | Strande ........................ 23/253 R X |
| 3,782,548 | 1/1974 | Bowen ......................... 210/DIG. 23 |
| 3,785,367 | 1/1974 | Fortin et al. ................ 128/2 F |
| 3,837,376 | 9/1974 | Brown et al. ................ 210/540 X |
| 3,846,077 | 11/1974 | Ohringer ...................... 210/DIG. 23 |
| 3,852,194 | 12/1974 | Zine, Jr. ...................... 210/83 |
| 3,865,731 | 2/1975 | Seitz ............................ 210/DIG. 23 |
| 3,867,923 | 2/1975 | West ............................ 128/2 F |
| 3,905,528 | 9/1975 | Maiocco ...................... 210/DIG. 23 |
| 3,920,549 | 11/1975 | Gigliello et al. ............ 210/DIG. 23 |
| 3,926,521 | 12/1975 | Ginzel ......................... 128/2 F X |
| 3,960,727 | 6/1976 | Hochstrasser ............... 210/DIG. 23 |
| 4,052,320 | 10/1977 | Jakubowicz ................. 210/516 |

Primary Examiner—Richard L. Chiesa
Attorney, Agent, or Firm—Dana M. Schmidt

[57] ABSTRACT

A device for collecting and dispensing non-pressurized liquids, comprising a collection compartment having a capillary passageway extending from an intake and along the entire sample collection length of the compartment, and a dispensing chamber.

24 Claims, 15 Drawing Figures

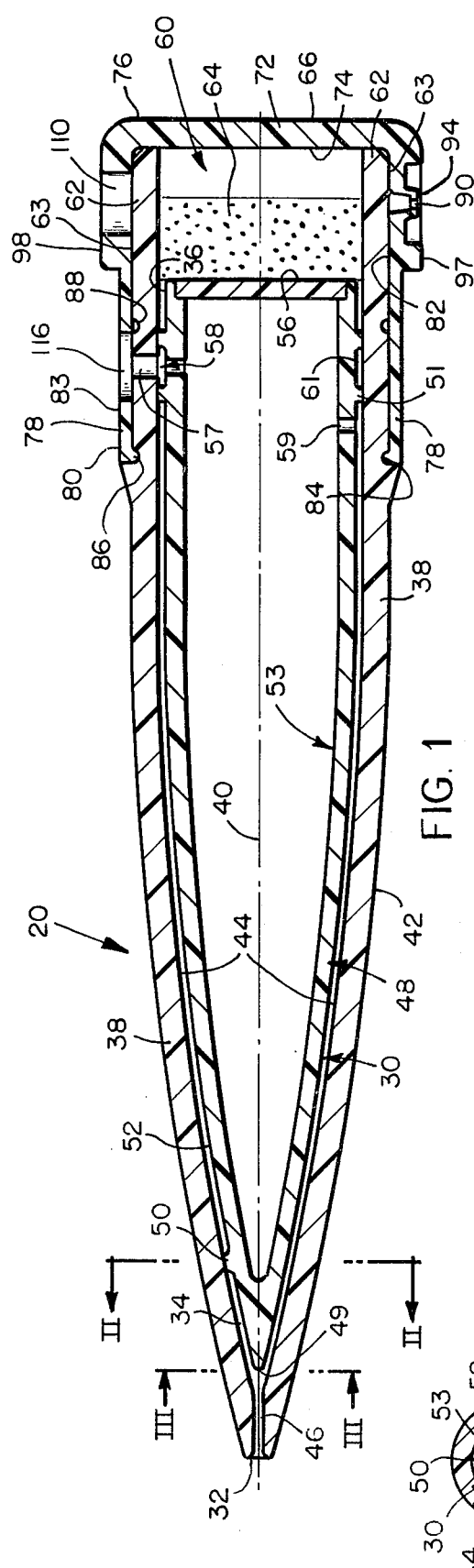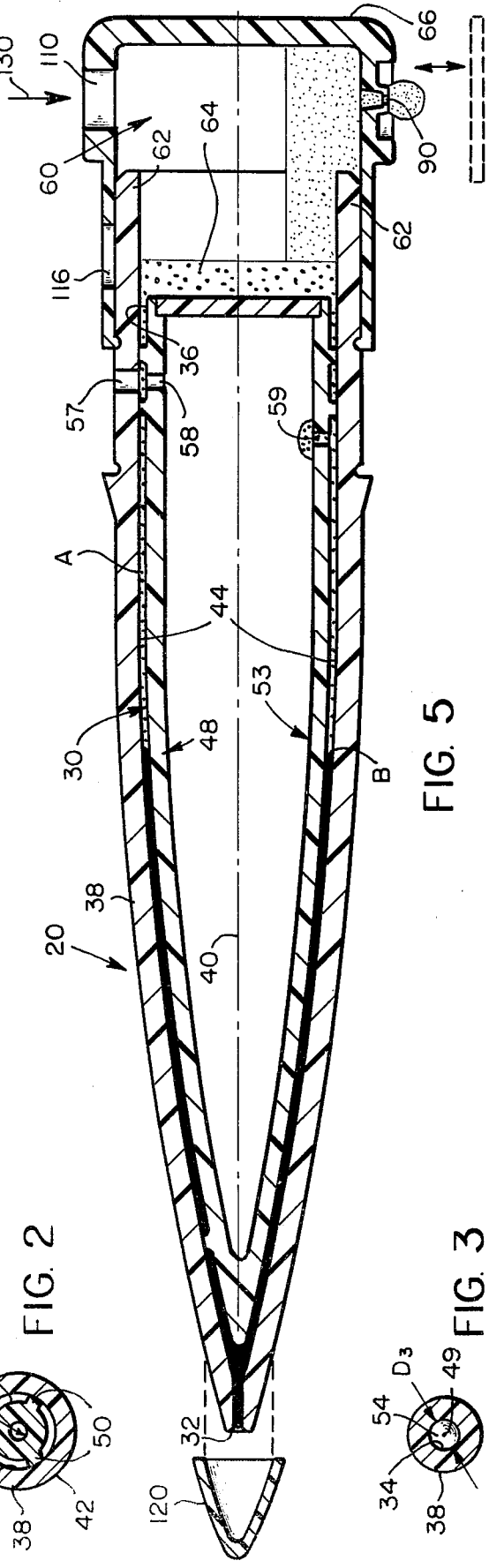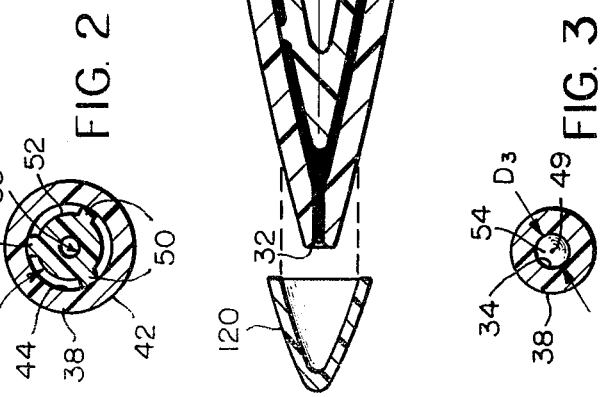

COLLECTION AND DISPENSING DEVICE FOR NON-PRESSURIZED LIQUIDS

RELATED APPLICATIONS

This application is a continuation-in-part application of U.S. application Ser. No. 674,462 filed on Apr. 7, 1976, and now abandoned.

BACKGROUND OF THE INVENTION (1) Field of the Invention

This invention relates to a device for the collecting and dispensing of non-pressurized liquids, such as puddled liquids or those in an open container. In the case of blood, the preferred liquid for collection, the device is particularly suited to collect from a non-venous source, such as blood drops drawn by a pin prick.

(2) State of the Prior Art

Of the many devices available to provide blood serum for analysis, the one which has become the norm is the evacuated container. This is simply a partially evacuated glass tube openable at one end except for a septum placed there. One improvement over such an evacuated container which is particularly useful comprises such a glass tube with a movable plug contained within the tube. The plug is preferably a silica gel, with or without a plastic cup-like mandrel positioned with its open end pointed to the septum. By reason of the vacuum, collected blood is easily drawn into the container. The container is then spun about a centrifuge axis adjacent to the septum end, and the gel by reason of its selected specific gravity works up to the serum-cell interface where it plugs the container against remixing of the serum and cells. An example of such a container but without the mandrel is shown in U.S. Pat. No. 3,852,194.

Although such a device is useful in separating the serum from the cells, it has not avoided the transfer difficulties by which the separated serum is obtained. That is, after centrifuging, the serum is commonly poured off into yet another container for the desired clinical testing. All such transfer operations are time consuming, requiring either hand processing or complicated, expensive automatic handling. Furthermore, whenever there is a transfer of a liquid sample to a separate, open container, the sample is aerated and $CO_2$ loss or gain can occur. There is also the danger of improper transfer, either by the use of the wrong container, by the improper patient labeling of the new container, or by both. Still further, contamination of the serum by foreign materials can occur, including for example, contamination by blood cells collected at the septum-container interface prior to centrifuging, a condition known as "blood-ring contamination".

Still other drawbacks concerning evacuated containers are that the rapid intake tends to cause hemolysis by reason of the high shear rate, particularly when flow is through reduced diameters; the vacuum can cause collapse of the patient's vein; and occasionally the containers become "flat", i.e., they lose their vacuum. In such a case of a "flat" container, the broken seal is generally insufficient to create a truly vented configuration, so that the hydrostatic pressure of the veins from which the blood is drawn encounters back pressure, and the rate of fill is insufficient. When the container is formed from solid glass, it is not possible prior to actual use to determine the loss of vacuum merely by visual inspection, and the result is that the patient has to wait while the technician looks for a new, hopefully evacuated, container.

Yet another disadvantage of such evacuated containers is that they are generally used to collect relatively large volumes, on the order of about 5–10 ml. Since the serum and cells are separated within this volume by centrifuging, a small fraction cannot be efficiently collected. However, certain classes of patients cannot spare this amount of blood, including both the elderly and the infant. To deal with this problem, simple capillary draws have been used on pin pricks. Dispensing of serum from such draws is difficult, however. Furthermore, a device capable of collecting blood volumes intermediate the minimum amount typified by capillary draws and the large amount by evacuated containers is desirable.

As a means of collecting intermediate amounts, a capillary tube has been connected to a larger container of the type shown, for example, in U.S. Pat. No. 3,640,267. These devices do provide a reduced volume collection, such as for the elderly. Although the U.S. Pat. No. 3,640,267 provides for non-venous collection devices, such devices are not suitable for serum separation in the same container. Furthermore, such devices use a collapsible membrane which requires the operator to repeatedly actuate the device. A preferred construction is one in which no operator effort needs to be expended.

U.S. Pat. No. 3,645,252 also discloses a device to collect more than the minimum amount, but less than the collection capacity of evacuated containers. However, vacuum again is resorted to in such devices, and the utility is stated to be for venous sources, rather than non-venous.

Yet another disadvantage with conventional capillary draws is that, conventionally, serum is removed therefrom only after phase separation is complete, and then by pressurization or vacuum aspiration, as shown for example in U.S. Pat. No. 3,763,705. Such techniques tend to disturb the interface of the phase separation. Any device which disposes serum for dispensing outside of the capillary passageway as a part of the phase separation step would both reduce the number of processing steps and avoid disturbing the interface.

A vented, non-venous collection device has been disclosed, for example, in U.S. Pat. No. 3,926,521 issued Dec. 16, 1975, which uses a capillary tube connected by a frangible, tapered neck to a tube suitable for centrifugal blood separation. However, the capillary passageway terminates at the neck, so that only by positioning the device below the pooled blood can blood continue to flow by gravity into the device to fill it. The device cannot be located above the source.

Mild obstructions have been placed in blood collecting devices for various purposes other than for creating a capillary effect at the obstruction to fill the container. For example, the pipette shown in U.S. Pat. No. 3,741,732 has capillary flow along its entire length, and the obstruction by its hydrophobic nature is designed to terminate rather than assist flow. However, the entire contents are to be dispensed at once, so that no separate dispensing chamber or means for displacing liquid into the chamber are provided for.

In the syringe disclosed in U.S. Pat. No. 2,941,869, a coiled wire is disposed in a tube solely to hemolyze the blood flowing past it. Nowhere is capillary flow discussed.

Blood flow devices having capillary restrictions at a portion intermediate the ends thereof have been constructed not for the purpose of collecting blood and for separating serum, but rather for blood cell counting, as shown for example, in U.S. Pat. Nos. 2,369,577; 2,779,232; 2,807,416 and 2,875,666. These devices are not intended for, nor are they capable of, use as non-pressurized serum collectors and separators as there is no provision, for example, for capillary flow extending the entire sample collection length.

Flexible containers have been used to collect whole blood, and by reason of their flexibility, they may have capillary passageways somewhere defined when the walls are collapsed. However, the collapsed wall condition is designed not to fill the containers by capillary action, but rather either to create a vacuum which causes filling of the container, as shown for example, in U.S. Pat. No. 3,513,829, or to indicate whether desired arterial blood as opposed to undesired venous blood is being collected, as shown for example in U.S. Pat. No. 3,785,367.

U.S. Pat. No. 3,867,923 is representative of blood collection bags which are completely collapsed along their entire length, and which therefore initially provide a capillary passageway along their entire length. However, such devices lose their effective capillary as soon as blood enters. Because they are not vented to the atmosphere, they require the patient's blood pressure to expnd the device into its full volume. They cannot be used to collect non-pressurized blood.

Patents relating generally to the background of blood collection include for example U.S. Pat. No. 3,610,226.

(3) Related Applications

In U.S. application Ser. No. 545,670, filed on Jan. 30, 1975, entitled "Metering Apparatus", now abandoned and refiled and issued as U.S. Pat. No. 4,041,995, there is disclosed a dispenser chamber uniquely designed to dispense microvolume drops, one at a time, of fluids of variable properties such as blood serum. In U.S. Pat. No. 4,012,325 issued on application Ser. No. 581,345, filed on May 27, 1975, a CIP of application Ser. No. 539,577, filed on Jan. 8, 1975, now abandoned, entitled "Biological Fluid Dispenser and Separator", there is disclosed a combined serum separator and dispenser which preferably draws in blood at one end and collects and dispenses drops of serum at the other, whereby blood ring contamination can be avoided. The device can be vented or evacuated.

In U.S. Pat. No. 4,052,320 issued on Oct. 4, 1977 on commonly owned U.S. application Ser. No. 703,476, filed on July 8, 1976, a continuation-in-part application of Ser. No. 609,121 filed on Aug. 29, 1975 by R. F. Jakubowicz, entitled "Telescoping Serum Separator and Dispenser", there is disclosed a combined serum separator and dispenser wherein the dispensing chamber telescopes with respect to the serum separating compartment to open or close flow of serum from the separating compartment to the dispensing chamber.

In U.S. application Ser. No. 658,208, filed on Feb. 17, 1976, and now U.S. Pat. No. 4,091,182, entitled "Vented Liquid Collection Device", there is disclosed a vented collecting and dispensing device which uses a capillary passageway along a portion of the sample collection length of the collection compartment to increase the speed of collection. The prime mover of the blood in such a device is the veinal pressure of the patient.

OBJECTS OF THE INVENTION

It is an object of the invention to provide a liquid collection and dispensing device which internally provides the collection force necessary to collect non-pressurized liquids, but without the use of a vacuum and without requiring the operator to generate the force.

It is another object of the invention to provide such a device wherein the total collected volume is small, i.e., on the order of 500 $\mu$l or less.

A further object of the invention is to provide such a device with a dispenser capable of accurately and repeatedly dispensing only a portion of the collected serum.

A related object is to provide such a capillary device which will collect a volume intermediate the minimum collected by simple capillary tubes and that required for evacuated cylinders.

Other objects and advantages will become apparent upon reference to the following Summary and Detailed Description when read in light of the attached drawings.

SUMMARY OF THE INVENTION

The invention concerns a collection device which mechanically provides the collection force for non-pressurized liquids, without the use of a vacuum. According to one aspect of the invention, there is provided a vented liquid collecting and dispensing device for collecting non-pressurized liquids, comprising a collection compartment having an intake end, a discharge end generally opposite to the intake end, and at least one capillary passageway extending the entire sample collection length of the compartment from the intake end; a dispensing chamber adjacent the discharge end; a vent passageway extending from an inlet end adjacent to the discharge end to an outlet end on the exterior surface of the device; means for displacing liquid from the capillary passageway into the dispensing chamber; and means for sealing off the vent inlet end after collection is completed.

According to another aspect of the invention, there is provided a vented liquid collecting, separating and dispensing device for collecting, separating and dispensing non-pressurized liquids, comprising a collection compartment having an intake end, a discharge end generally opposite to said intake end, wall means connecting said ends to define with said ends the interior of said compartment, and capillary means in said compartment for drawing non-pressurized liquid into said compartment at said intake end by capillary attraction, said capillary means including a core contained within said compartment which converts said interior into a liquid flow path through which the liquid is drawn by capillary attraction, the cross-sectional area of said flow path, measured transversely to said flow at any point along the length of said interior, being at least 4(1 + d/t) times the cross-sectional area of a capillary flow path in a hypothetical chamber lacking said core, where "d" is the diameter of said core, and "t" is the maximum dimension transverse to liquid flow in said flow path of either said compartment or said hypothetical chamber, and is no larger than that which will support capillary flow, a dispensing chamber adjacent and in fluid communication with said discharge end, a vent passageway extending from an inlet end adjacent to and in fluid communication with said discharge end to an outlet end on the exterior surface of the device, to exhaust air from said compartment as liquid is drawn in, and means for displacing liquid from said capillary passageway into said dispensing chamber in response to a centrifugal force.

BRIEF DESCRIPTION OF THE DRAWINGS

FIG. 1 is an elevational view sectioned along its axis of symmetry of a device constructed in accordance with the invention;

FIGS. 2 and 3 are cross-sectional views taken generally along the lines II—II and III—III of FIG. 1;

FIG. 5 is a view similar to FIG. 1, but illustrating the dispensing mode of the device;

DESCRIPTION OF THE PREFERRED EMBODIMENTS

Figure 4:
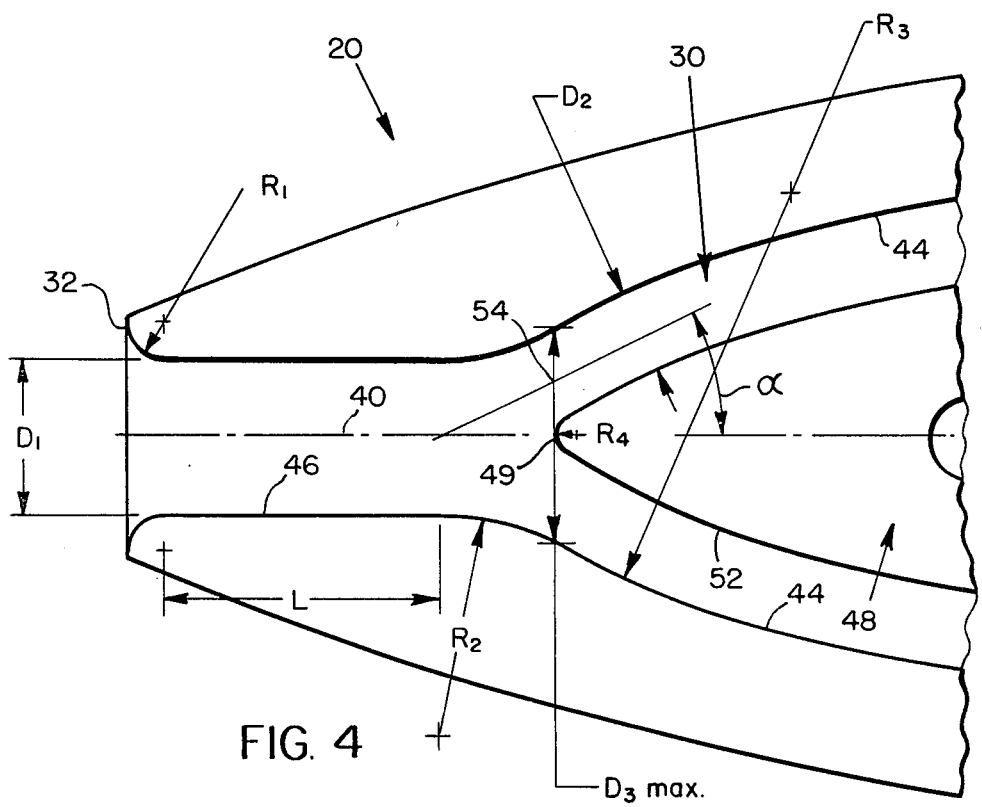
FIG. 4 is an enlarged, fragmentary sectional view of the intake portion of the device shown in FIG. 1.

Although the invention is hereinafter described by reference to embodiments showing the collection and dispensing of blood serum, it is not limited thereto. Rather, it can be used to collect and dispense any non-pressurized liquid.

In accordance with one aspect of the invention, the device herein described provides internally the collection force for the non-pressurized liquid through the use of a liquid flow path featuring at least one capillary passageway extending the entire sample collection length of the collection compartment from the intake end of that compartment. No operator force is required. As used herein, "sample collection length of the compartment" refers to the length of the collection compartment which is occupied by the liquid, preferably blood, after it is collected. Because only capillary forces are used for the collection, the sample collection length is thus confined to the capillary passageway(s) and terminates when the capillary dimensions terminate. Preferably, such termination point is located at least about 90% along the length of the collection compartment from the intake end.

As used herein, "capillary force" or "capillary effect" refers to the force or phenomena obtained when the free surface of the collected liquid, because of surface tension, moves along the confining walls to draw in more liquid until a head of liquid is achieved in which gravity prevents further increase in liquid volume, or until the source of liquid is removed. It is because of the gravitational limits that the length of a capillary passageway cannot be increased at will to achieve increased volumes.

In accordance with another aspect of the invention, a capillary collection device is provided which achieves increased capacity without increasing the overall length of the device. To achieve this, a core is preferably positioned within the collection compartment so that the capillary passageway becomes an annular capillary volume, as distinguished from a column of liquid. Preferably, the liquid to be collected first enters a capillary entrance at the intake end of the device, and thereafter forms the capillary volume when it encounters the core endpoint. However, in some instances the entrance can be omitted so that the annular volume commences immediately at the intake end. The "flow-through aperture of the capillary volume" is the aperture obtained in a plane tangent to the core endpoint, and which is perpendicular to the flow within the capillary entrance, if used. The liquid flowing through this aperture away from the entrance has a definable direction of flow determined by the shape of the effective capillary walls, and when measured at any midpoint of the annular capillary volume in the flow-through aperture between the core endpoint and the effective outer capillary wall, this direction is referred to as the "flow divergence direction".

In accordance with another aspect of the invention, the device herein described provides a dispensing chamber utilizing a valve such as that disclosed in the aforesaid Ser. No. 581,345, the chamber being modified to accommodate the reduced volume of serum that is provided.

Terms of orientation such as "up", "down" and the like refer to orientation of parts during actual use.

After the collection, separation and dispensing of blood serum by this device, individual drops of the serum can be deposited for analysis onto a suitable substrate, shown in phantom, FIG. 5, of which those shown for example in Belgian Pat. No. 801,742 granted on Jan. 2, 1974, can be used.

Turning now to FIGS. 1–3, the device 20 of the invention comprises a collection compartment 30 extending from an intake end 32, through an annular capillary volume 34 to a discharge end 36, and a dispensing chamber 60 adjacent to end 36.

The collection compartment shown in FIG. 1 comprises a capillary passageway formed within walls 38, which as shown can be a single wall circumscribing the passageway. Preferably, walls 38 are symmetrically disposed about an axis 40, with an outside surface 42 defining an outer diameter for walls 38 which increases as the distance from intake end 32 increases. The inner surface 44 of walls 38, also of increasing diameter, partially defines the shape of compartment 30 and is the effective outer wall of most of the capillary passageway.

To insure that compartment 30 has a capillary passageway for its entire sample collection length, i.e., one in which a capillary effect will be maintained, the capillary entrance 46 of the passageway immediately inside intake end 32 has dimensions no larger than those which will permit the capillary effect. Further, a liquid-impermeable core 48 is disposed by discontinuous spacer members or ribs 50 and 51 between the inner surfaces 44 and spaced therefrom a distance no greater than that which will maintain a capillary effect, along the entire sample collection length. The compartment volume is thus altered from tubular volume in the capillary entrance to an annular capillary volume around the core, initiated at one end 49 of the core. Outer surfaces 52 of the core are preferably concentric with, and thus determined by the shape of, surfaces 44 of walls 38, and form the effective inner wall of most of the capillary passageway. Thus core 48 can have any shape, that of FIG. 1 being generally conical. For convenience in manufacturing, as well as to trap excess blood as described hereafter, the core is preferably hollow with a compartment 53 extending a substantial portion of its length.

Turning now to FIG. 4, the dimensions of compartment 30 which are important to maintain the capillary effect are: the maximum dimension $D_1$ transverse to flow through entrance 46; the transition from $D_1$ to the annular capillary volume particularly as defined by the ratio of the maximum dimension $D_3$ of the flow-through aperture of the capillary volume at the point of formation of such volume, to $D_1$; the flow divergence direction in the flow-through aperture, measured as a cone angle diverging from the direction of the capillary entrance 46; and the maximum spacing of the core 48 from inner surface 44 measured transversely to the flow through the annular volume.

Considering first $D_1$, dimensions in the range of about 0.05 cm to about 0.12 cm have been proven successful, with 0.1 cm being preferred. Conveniently, entrance 46 is cylindrical so that $D_1$ is a diameter, and entrance 46 has an axis parallel to, and concentric with, axis 40. The radius $R_1$ of intake end 32, although not critical, should be greater than about 0.01 cm to permit pooling of the blood and a gradual access to the capillary entrance.

With regard to the transition of $D_1$ to $D_3$, it should be gradual as caused by generous radii $R_2$ and $R_3$ for surfaces 44, i.e., radii preferably larger than about 0.04 cm. The ratio of $D_{3max}$ to $D_1$ should be no larger than about 2.5/1 to avoid breaking the capillary effect. Preferably, such ratio is about 1.5/1. It will be appreciated that the lower the value of $R_2$, the smaller this ratio must be. It is not essential, however, that $D_3$ of the flow-through aperture occur exactly at the transition between $R_2$ and $R_3$.

As noted above, the flow divergence direction, as defined above, is measured at a midpoint 54 in the plane tangent to end 49 of core 48 and perpendicular to the direction of flow through entrance 46, FIGS. 3 and 4. A three-dimensional cone angle $\alpha$ is formed by extrapolating the flow divergence direction back to the axis 40. Preferably that angle is less than about 45°. A convenient value of $\alpha$ is about 10°. Practicality, of course, dictates that the cone angle preferably decreases as the distance from end 32 increases.

The surfaces 44 and the surfaces 52 can have a variety of radii $R_3$ for the length of compartment 30. The more important dimension is $D_2$, the depth of capillary flow, which preferably conforms to the limits noted for above for $D_1$. The actual chosen value will depend in part on whether the intended use of device 20 contemplates a constant vertical orientation, in which case lower values of $D_2$ should be used, particularly if the length of compartment 30 is to be relatively large. $D_2$ is of course maintained the entire sample collection length of compartment 30, which length is preferably at least about 90% of the distance of the compartment from intake end 32. As shown in FIG. 1, the sample collection length ends at point A. Beyond this point, the compartment 30 can be enlarged beyond that which will support a capillary effect, until discharge end 36 is reached. The discharge end 36 of compartment 30 coincides with an end plate 56 of the core 48.

Still another aspect of core 48 which affects the capillary flow is the shape of end 49. A flat end is undesirable as the edge effects would impede capillary flow. The value of the radius of curvature $R_4$ for end 49 should be such as to give a minimum obstruction to the incoming blood flow. As will be appreciated, the larger the value of $D_1$, the larger can be the value of $R_4$.

Typical values for the dimensions discussed above, which are representative and nonlimiting, are set forth in Table 1, for an overall length of compartment 30 of about 5 cm.

Table 1

$D_1$ = 0.1 cm
$D_2$ = 0.045 cm
$R_1$ = 0.05 cm
$D_3$ = 0.127 cm
$R_2$ = 0.119 cm
$R_3$ = 0.026 cm
$\alpha$ = 4°
$R_4$ = 0.027 cm Sample Collection Length to Point A = 4.6 cm It will be appreciated that the annular capillary volume greatly increases the amount of blood that can be collected within the walls of the compartment, over that capable of being collected in a single capillary tube, the conventional approach. At the same time, the overall length of the device is kept within manageable bounds and within the gravity restraints on capillary columns. Specifically, although the volume, and therefore the cross-sectional area, transverse to flow is reduced by the space occupied by the core, compared to the overall cross-sectional area of the compartment, nevertheless the cross-sectional area is greater than the area obtained by multiplying the maximum compartment dimension between wall surfaces 44, by the maximum depth of sustainable capillary flow. Such latter cross-sectional area is that which is obtainable if a flat compartment is used, lacking a core, of a width equal to the aforesaid maximum compartment dimension and a height equal to the maximum depth of sustainable capillary flow.

A more precise comparison can be expressed in that it can be shown that the cross-sectional flow-through area $A_c$ of the "cored" compartment of the invention, taken anywhere along the length of the compartment, is at least $4(1 + d/t)$ times the area $A_e$ of an "empty" hypothetical cylindrical chamber having a capillary flow path $P_e$ lacking the core. In this analysis, "d" is the diameter of the core and "t" is the maximum depth of sustainable capillary flow ($D_2$ for the "cored" compartment shown in FIG. 4), measured transverse to flow in either the compartment or the hypothetical chamber, "t" being no larger than that which will support capillary flow. As used herein, "flow path" refers to the total flow pattern provided by all of the capillary passageways taken together. The passageway $P_e$ has a diameter $D_e$ which is also assumed to be maximized, that is, is the largest that is possible without destroying the capillary effect. Except where hereinafter noted, it is also assumed that $d \neq 0$, that is, a core is present with a finite diameter, in the analysis of $A_c$.

(1) Thus, for the hypothetical empty cylinder, $$A_e = \frac{\pi (D_e)^2}{4}.$$

(2) For the device containing the core, for example, device 20 as shown in FIG. 1, $$A_c = \frac{\pi}{4}(D_c{}^2 - d^2) \text{ or}$$

$$A_c = \frac{\pi}{4}(D_c - d)(D_c + d)$$

where $D_c$ is the overall diameter, i.e., is equal to $d + 2t$.

(3) Because $D_3 - d = 2t$, $$A_c = \frac{\pi}{4}(2t)(D_c + d).$$

(4)

$$\frac{A_c}{A_e} = \frac{2t(D_c + d)}{(D_e)^2}.$$

(5) Since $D_c = 2t + d$, $$\frac{A_c}{A_e} = \frac{2t(2t + d + d)}{(D_e)^2}$$

$$\frac{A_c}{A_e} = \frac{4(t^2 + dt)}{D_e{}^2}$$

$$\frac{A_c}{A_e} = \frac{4t^2(1 + d/t)}{(D_e)^2}.$$

Because $D_e$ and $t$ are considered to be the dimension beyond which capillary attraction ceases, one can assume $D_e = t$ except at $d = 0$.

(6) Therefore, except at $d = 0$, $$\frac{A_c}{A_e} = 4(1 + d/t)$$

and at $d = 0$ (not of interest in most cases), $D_e = D_c = 2t$ and $$\frac{A_c}{A_e} = \frac{\frac{4D_e{}^2}{4}(1 + 0)}{D_e{}^2} = 1,$$

as it should. Thus, the cross-sectional area of the flow path is increased by $4(1 + d/t)$ times the cross-sectional area of the path available in the noted hypothetical chamber lacking the core, that still uses capillary attraction as the flow-generating force.

Figure 6:
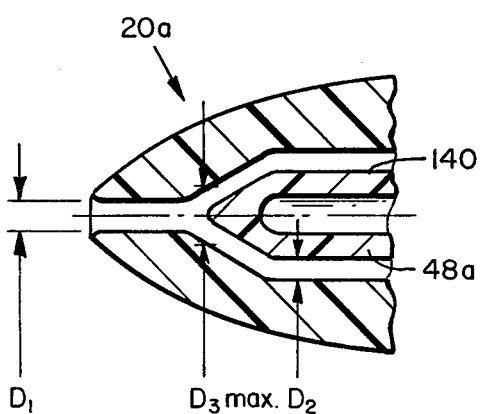
FIGS. 6 and 7 are fragmentary sectional views similar to FIG. 5 but illustrating alternative embodiments.

(7) An illustrative device similar to that shown in FIG. 6 would have a value of $t = 0.045$ cm ($D_2$ of Table 1) and $d \approx 0.5$ cm, or $d/t \approx 0.5/0.045 \approx 10$ to 1. For this value, disregarding the entrance capillary volume, the efficiency is $$\frac{A_c}{A_e} = 4(1 + 10) = 44,$$

compared to a cylindrical, empty chamber of diameter $t$. For core embodiments which are conical in nature, or hollow (FIG. 9), an even greater efficiency results, due to the increasing value of $d$ ($t$ remains constant), or due to the volume contained within the core, respectively.

To vent or exhaust trapped air in the device to the atmosphere, an aperture 57, FIG. 1, is formed in walls 38 and an aperture 58 in member 51, both being adjacent to discharge end 36. To avoid alignment problems, discontinuous spacer member 51 is provided with a slot 61 to permit continuous air flow from aperture 58 to aperture 57 even if the two apertures are not aligned. An additional inlet end aperture 59 is formed in the wall of the core generally opposite to aperture 58, thereby forming a vent passageway extending from aperture 59 through aperture 58 to aperture 57. An additional vent aperture in container 66, discussed hereinafter, serves as the outlet end of the vent passageway. The vent passageway thus permits air which is trapped by the incoming blood to be expelled from the device. Because the vent passageway extends through the core, the internal compartment 53 also acts to trap any excess blood which might enter into inlet end 59 during the blood collection.

The ends 62 of walls 38 extend beyond discharge end 36 to define a portion of the dispensing chamber 60. Disposed initially within the chamber between ends 62 is a movable phase separator 64. The separator can either be disposed against end plate 56 as shown, against end wall 72 hereinafter described, or it can fill the entire chamber 60. This separator preferably comprises a silica gel which can be a blend of hydrophobic silicon dioxide and a silicone, such as dimethylpolysiloxane, blended to give a thixotropic gel having a specific gravity between about 1.035 and 1.06, and preferably about 1.04–1.05, and a viscosity between about 400 and about 500 poise at a shear rate of about 500 sec.$^{-1}$, and typically 451 poise at 506 sec.$^{-1}$. The gel preferably is used by itself without a mandrel, and can be the type taught for example in U.S. Pat. No. 3,852,194.

The remaining portion of the dispensing chamber 60 comprises a sliding container 66 mounted over exterior surfaces 63 of ends 62. As disclosed in the aforesaid Jakubowicz application, container 66 comprises an end wall 72 having an interior side or surface 74 and an exterior side or surface 76, and opposed side walls 78 extending from side 74, terminating at an opposite end 80 of the container 66. The side walls 78 accommodate or encompass ends 62, so that these ends are movably mounted and preferably telescoped within end container 66. A particularly useful configuration is one in which the opposed walls 78 are arranged about an axis which is coincident with axis 40. Thus, as with the other compartments, the walls 78 can have a shape in which the walls form one continuous wall.

The walls 78 have an interior surface 82 and an exterior surface 83. The interior surface 82 preferably matches the shape of ends 62. Between the interior surfaces is the interior of the container 66. That interior is temporarily blocked from fluid flow of serum from end compartment discharge 36 by virtue of the removable seal formed by side 74 of end wall 72 positioned against ends 62. The device 20 is further provided with means for sealing the interior of end 80 of container 66 against head 62, and for slidably moving the container to an open dispensing position. The means permitting the movement of container 66 between the two positions is the approximate coincidence of the interior diameter of surface 82 of container 66 and the exterior diameter of ends 62. Flexibility of walls 78 permit a circumferential rim 86 of end 80 to ride across the surface of ends 62. A preferred form of the sealing means is a groove 84 extending around the entire circumference of head 62, shaped to mate with rim 86 of end 80. An additional groove 88 can be added to head 62 to increase the airtight seal during the dispensing operation, if desired.

Preferably, two apertures 90 and 110 are formed in the side walls 78, for the dispensing operation hereinafter described. For aperture 90, the side wall 78 had a specially-constructed drop-forming platform 94 isolated from the rest of the exterior surface 83 by a connecting portion or surface, and surrounded by a protecting shoulder 97. Conveniently, such shoulder 97 is part of a ring 98 extending around the circumference of head 62. Aperture 90 is centered within the platform 94.

The function of the platform 94 and aperture 90 is to accurately form successive, pendant drops of predictable and uniform volume, each of which is to be touched off on a suitable substrate. To provide this function with a fluid having such drastically varying properties as blood serum, certain features have been found to be useful. Thus, platform 94 is preferably vertically separated from the surface 83 by a minimum distance, and horizontally separated from shoulders 97 by a minimum width. Further, aperture 90 preferably has a maximum dimension at the exterior surface of platform 94, measured transversely to fluid flow therethrough, which is less than that which will permit flow of blood serum under the influence of gravity and which is large enough to retard closure of the aperture by protein agglomeration; the intersection of the aperture 90 with the platform surface preferably is essentially a sharp edge, i.e., having a radius of curvature no greater than about 0.02 cm; and the transition zone between platform 94 and the connecting surface defines an edge which preferably is sufficiently sharp as to prevent the tendency of the serum drop to climb up the connecting surface under the influence of surface tension. The actual values for each of these features of container 66, and other desirable aspects of the dispensing container 66, including the accurate, repeatable dispensing achieved threfrom, are disclosed in *Research Disclosure*, Vol. 133, Publication No. 13360, May 1975, the details of which are hereby incorporated by reference.

Aperture 110 of side walls 78 is preferably positioned opposite the aperture 90, and need otherwise be constructed only as a passageway for pressurized gas generated exterior to the container.

A vent aperture 116 is positioned in side walls 78 so as to be aligned with aperture 57 when rim 86 is seated in groove 84, to complete the venting of the device to the atmosphere during blood collection.

The entire device 20 can be made from any suitable material, of which molded synthetic rigid polymers or "plastics" are useful examples. For example, a rigid "Saran" vinyl chloride-vinylidene chloride copolymer manufactured by Dow Chemical Company is one preferred example. At least walls 38 and 48 of compartment 30 should be made from a polymer that will be wetted by the collected liquid, such as various polyesters, polystyrene, and various acrylics, or by hydrophobic plastics coated with a surfactant that is nonreactive with the collected blood.

An appropriate patient identification mark or symbol can be placed or otherwise formed at or on any exterior surface of the device.

FIG. 5 illustrates the steps in the use of device 20. An optional cover 120 is removed from intake end 32 and a puddle of blood is drawn by capillary effect into entrance 46, through the flow-through aperture at end 49, all the way to the end, designated as "A", of the compartment sample collection length. Trapped air is expelled through the vent passageway, and excess blood, if any, enters aperture 59 to be retained in compartment 53. The phase separator gel is initially located in the dispensing chamber 60, as shown in FIG. 1, and it can completely fill the space between ends 62 and between wall 72 and plate 56.

Collection of blood terminates when device 20 is removed from the source of blood. Thereafter, phase separation of the serum is achieved by centrifuging the device, with cover 120 on, so that the centrifugal force is directed from chamber 60 towards end 32 along axis 40. As this occurs, gel 64 flows into compartment 30, its thixotropic characteristics permitting the lighter, serum phase to flow past it into chamber 60. The gel thus acts as a means for displacing the serum out of the capillary passageway between the core 48 and surfaces 44 of walls 38. Without such displacement, the serum is difficult to remove because of the capillary effect. After centrifuging is complete, substantially all the serum is in chamber 60, the gel 64 has sealed off compartment 30 adjacent discharge end 36 as well as aperture 59, and the undesirable blood cells are in the intake end of compartment 30, from end 32 to point "B", FIG. 5.

Thereafter, container 66 is slid or otherwise telescoped away from ends 62 to unblock apertures 90 and 110. Air pressure generated by suitable means in appropriate amounts in the direction of arrow 130, through aperture 110 causes the formation of a pendant drop, which can be touched off onto a suitable substrate. Details of such drop dispensing are disclosed in the aforesaid *Research Disclosure*. As noted in the Jakubowicz application, to insure that proper drop formation of predictable volume occurs the first time for a given pressure increase, the total air volume above the serum surface should be minimized. Such a feature can be particularly significant where, as here, the air volume is increased drastically before dispensing. It has been found that when the air volume above the serum in the container 66 opened to the extended position is about 1300 $\mu$l, for example, no problem occurs in accurate dispensing.

It will thus be seen that the device 20 relies entirely upon capillary forces to draw blood into it. By incorporating an annular capillary volume, the amount of blood is maximized over that which a single capillary draw can provide. During phase separation, the device automatically moves the serum into a dispensing chamber designed to dispense the same accurate portion of the total amount each time.

Alternatively, the amount of gel 64 can be decreased, so as to act only as a means for maintaining phase separation after centrifuging is completed. In such a case, the phase separation will result in the serum being located in compartment 30, adjacent end 36 thereof and not in the dispensing chamber. Displacement of the serum into the dispensing chamber can be achieved by connecting a source of pressure to intake end 32 and applying sufficient force, in gradually increasing amounts, to displace the separated blood clot and serum, en masse, along compartment 30 until most of the serum is located in the dispensing chamber. However, use of the gel to displace the serum is preferred, as such displacement of serum into the chamber occurs automatically, without a separate pressurizing step.

Turning now to FIGS. 6-9, here are illustrated alternate embodiments of the invention particularly concerning the core positioned within the collection compartment. Parts similar to those previously defined bear the same reference numeral to which the distinguishing suffixes "a", "b" and "c" are added, respectively. In FIG. 6, the device 20a is the same as in FIGS. 1-5, except that core 48a has a cylindrical portion 140 with a constant inner and outer capillary wall diameter, in contrast with the ever-increasing capillary wall diameters of the first-described embodiment.

Figure 7:
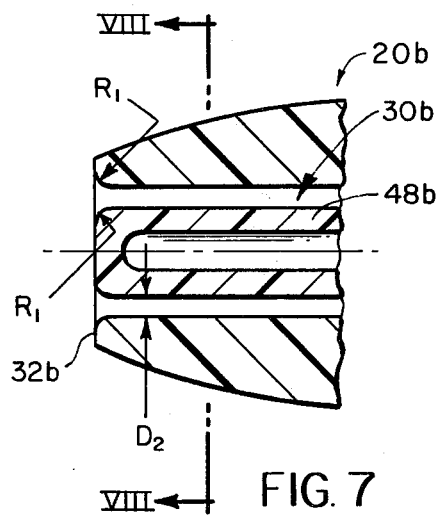
Figure 8:
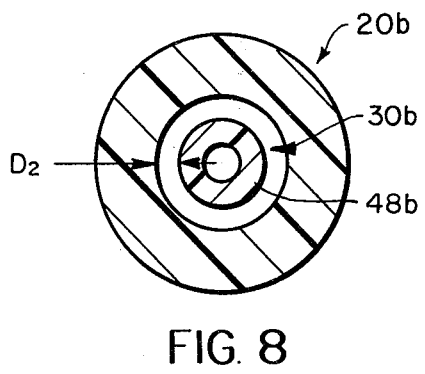
FIG. 8 is a sectional view taken generally along the line VIII—VIII of FIG. 7.

The device 20b of FIGS. 7 and 8 is similar to that of FIG. 6, except that the capillary entrance has been eliminated. Instead, intake end 32b comprises an annulus which flows straight back around core 48b to the dispensing chamber, not shown. In this embodiment, the width of core 48b at intake end 32b preferably is small enough to collect blood in the entire annulus from the same source. Alternatively, compartment 30b defined by the annular capillary passageway can have enlarged annular diameters with increasing distance from end 32b, simply by using the construction of FIG. 1, but with the entrance portion, i.e., passageway 46, eliminated.

Figure 9:
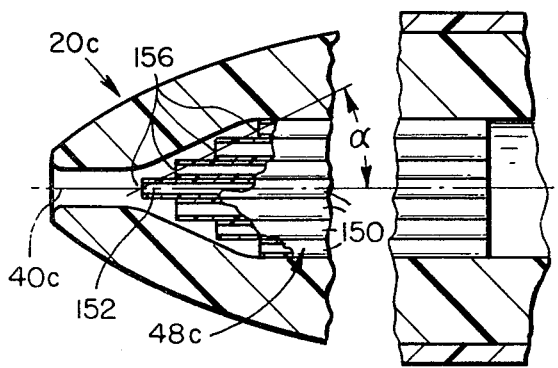
FIG. 9 is a fragmentary sectional view similar to FIG. 6 but illustrating yet another embodiment.

In FIG. 9, the cone angle formed by the flow divergence direction is formed by the use of a plurality of generally linear capillary tubes 150, stacked together to form the core 48c. The tube 152 in the center has the greatest length, with the tubes disposed outwardly from and concentrically around tube 152 having decreasing lengths, so that the midpoints 156 of the entrance of each tube are aligned along radii extending from the axis 40c to the outermost tube, to form a cone angle which diverges from the center tube outwardly from axis 40c to define angle α which is less than about 45°. Otherwise, the feature of device 20c are substantially the same as those of the embodiment shown in FIG. 6. The tubes 150 and 152 so arranged can be secured together by means such as adhesive.

Figure 10:
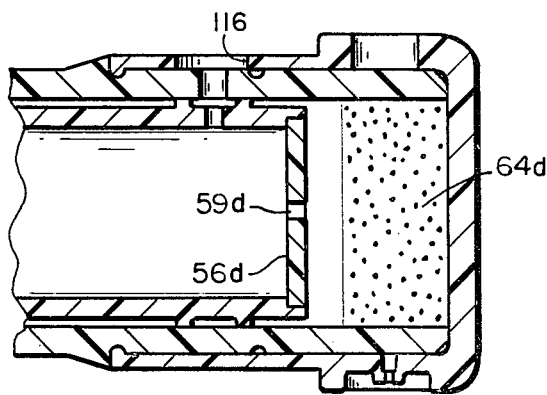
FIGS. 10 and 11 are fragmentary sectional views similar to FIG. 1, but illustrating other embodiments.
Figure 11:
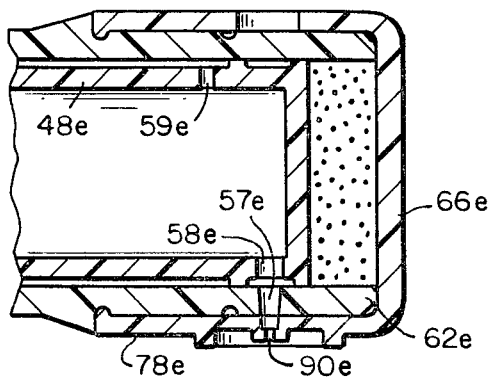
Figure 12:
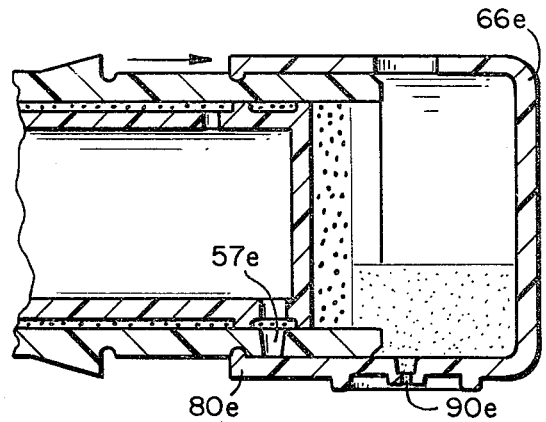
FIG. 12 is a fragmentary sectional view identical to the view of FIG. 11 but of the device in the dispensing mode.

FIGS. 10-12 illustrate alternative embodiments wherein the vent passageway has been altered. Parts similar to those previously described bear the same reference numeral to which the distinguishing suffixes "d" and "e" have been added. Thus, in FIG. 10, the vent inlet end is aperture 59d formed in end wall 56d. In such a case gel 64d is initially spaced away from the end wall so as to not plug aperture 59d until during the centrifugation step. In FIG. 11, aperture 90e in the container 66e forms the vent outlet end, so that aperture 116 can be eliminated from side wall 78e. The inlet end 55 aperture 59e of the vent passageway is located in the upper portion of core 48e, while aperture 58e is in the lower portion. Drop dispensing is achieved by sliding container 66e forward until aperture 90e clears ends 62e, end 80e however being long enough to block aperture 57e in walls 38e, FIG. 12, in this position.

Figure 14:
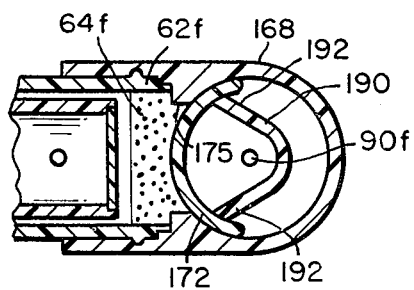
FIG. 14 is a cross-sectional view taken generally along the line XIV—XIV of FIG. 13.
Figure 13:
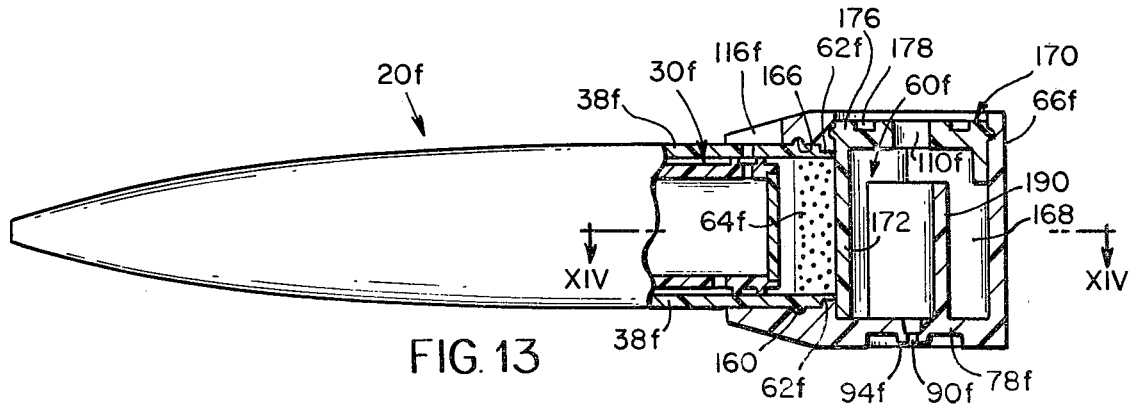
FIG. 13 is an elevational view in section similar to FIG. 1 but illustrating still another embodiment.
Figure 15:
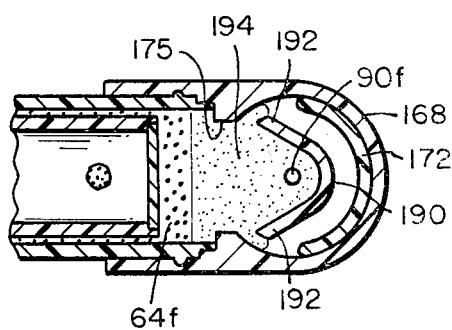
FIG. 15 is a sectional view similar to FIG. 14 but illustrating the dispensing mode.

FIGS. 13-15 illustrate yet another embodiment wherein the dispensing chamber is altered to include a rotatable valve. Parts similar to those previously described bear the same reference numeral to which the distinguishing suffix "f" has been applied. The collection compartment 30f of device 20f, and the collection procedure, are essentially the same as shown in FIG. 1. However, container 66f of chamber 60f has been modified so as to be nontranslatably mounted onto ends 62f of walls 38f, a protruding rim 160 of ends 62f fitting into a mating groove 166 in container 66f. The bottom wall 78f is the same as in previous embodiments, providing a drop-supporting platform 94f. However, the side walls 168, FIG. 14, are generally cylindrical and may be one continuous wall as shown, to accommodate a rotatable valve 170. Such a valve has a curvilinear valve stem 172 which fits against and slides with respect to walls 168. Stem 172 has a circumference subtending an angle sufficient to block flow of fluid past ends 62f through opening 175, FIG. 14. A top plate 176 is attached to the stem, and is provided both with suitable driving apertures 178 to rotate the valve, and pressurizing aperture 110f.

Thus, except for the valve stem and a partition 190 hereinafter described, container 66f is completely open to flow of serum through opening 175 from the space between ends 62f.

A vent passageway is formed as in the previous embodiments, the outlet end 116f being simply a portion removed from container 66f.

To minimize the surface area of, and the compressible air volume above, serum allowed to flow past opening 175 into container 66f, a partition 190 is affixed to wall 78f in arcuate arrangement about aperture 90f. The opposite ends 192 of the partition are angled towards the opening 175, but are spaced away from walls 168 by a distance that is sufficiently large as to permit passage of stem 172. At the same time, however, the spacing of ends 192 is sufficiently small as to create a blocking meniscus effect in blood serum which has flowed past opening 175, thus confining the serum between the opening 175 and partition 190, FIG. 15. A typical spacing to produce this meniscus effect is about 0.06 cm. Thus the thickness of the stem 172 must be less than this spacing.

The result is a column of serum of reduced surface area 194 confined between ends 192 of partition 190, requiring less pressure gradients for dispensing than would be the case in the absence of partition 190. Such a feature is particularly useful when the amount of serum presented within container 66f is reduced because of the initial reduced collection.

During the collection phase, gel 64f assists in blocking flow of liquid, if any, into container 66f, by being confined against stem 172 in opening 175, FIG. 13. As in the previous embodiments, during centrifuging the gel displaces the serum out of compartment 30f into chamber 60f between ends 62f.

The invention has been described in detail with particular reference to certain preferred embodiments thereof, but it will be understood that variations and modifications can be effected within the spirit and scope of the invention.

What is claimed is:

1. A vented liquid collecting, separating, and dispensing device for collecting, separating and dispensing non-pressurized liquids, said device comprising
a collection compartment having an intake end, a discharge end generally opposite to said intake end, wall means connecting said ends to define with said ends the interior of said compartment, and capillary means in said compartment for drawing non-pressurized liquid into said compartment at said intake end by capillary attraction, said capillary means including a core contained within said compartment which creates a path along the compartment for capillary flow of liquid, said path having a cross-sectional area that is less than that of said compartment but greater than the area obtained by multiplying the maximum compartment dimension between said wall means by the maximum depth of sustainable capillary flow, a dispensing chamber adjacent and in fluid communication with said discharge end, a vent passageway extending from an inlet end adjacent to and in fluid communication with said discharge end to an outlet end on the exterior surface of the device, to exhaust air from said compartment as liquid is drawn in, and means for displacing liquid from said capillary passageway into said dispensing chamber in response to a centrifugal force.

2. A device as defined in claim 1, wherein said displacing means comprises a thixotropic gel initially positioned within said dispensing chamber.

3. A device as defined in claim 1 wherein said dispensing chamber includes a platform suitable for the formation of pendant drops thereon, said platform including an aperture sufficiently small as to prevent gravitational flow of liquid therethrough.

4. A device as defined in claim 3 wherein said vent outlet end is said platform aperture.

5. A vented liquid collecting, separating, and dispensing device for collecting, separating and dispensing non-pressurized liquids, said device comprising a collection compartment having an intake end, a discharge end generally opposite to said intake end, wall means connecting said ends to define with said ends the interior of said compartment, and capillary means in said compartment for drawing non-pressurized liquid into said compartment at said intake end by capillary attraction, said capillary means including a core contained within said compartment which creates a path along the compartment for capillary flow of liquid, said path having a cross-sectional area that is at least $4(1 + d/t)$ times the cross-sectional area of a capillary flow path in a hypothetical cylindrical chamber lacking a core, where "d" is the diameter of said core, and "t" is the maximum depth of sustainable capillary flow, a dispensing chamber adjacent and in fluid communication with said discharge end, a vent passageway extending from an inlet end adjacent to and in fluid communication with said discharge end to an outlet end on the exterior surface of the device, to exhaust air from said compartment as liquid is drawn in, and means for displacing liquid from said capillary passageway into said dispensing chamber is response to a centrifugal force.

6. A vented liquid collecting and dispensing device for collecting non-pressurized liquids, comprising a collection compartment having an intake end, a discharge end generally opposite to said intake end, wall means connecting said ends and defining with said ends the interior of said compartment, and capillary means in said compartment for drawing non-pressurized liquid into said compartment at said intake end by capillary attraction, said capillary means subdividing said interior into at least one capillary passageway through which the liquid is drawn by capillary attraction, and including a core having spacer members which space the core away from said wall means a generally constant distance, a dispensing chamber adjacent and in fluid communication with said discharge end, a vent passageway extending from an inlet end adjacent to and in fluid communication with said discharge end to an outlet end on the exterior surface of the device, to exhaust air from said compartment as liquid is drawn in, and means for displacing liquid from said capillary passageway into said dispensing chamber.

7. A device as defined in claim 6 wherein said core is conical in shape, whereby said wall means has an outer diameter which increases from said intake end to said discharge end.

8. A device as defined in claim 6 wherein at least a portion of said core is cylindrical, whereby said effective outer wall has a diameter which remains the same along at least a portion of the length of said compartment.

9. A device as defined in claim 6 wherein said vent inlet end is an aperture in a wall of said core and a portion of said vent passageway extends through said core and through one of said spacer members.

10. A device as defined in claim 9 wherein said core terminates in an end wall adjacent said discharge end, said vent inlet end comprises an aperture in said end wall, and wherein said displacing means is initially disposed in said chamber but spaced away from said end wall.

11. A device as defined in claim 6 wherein said capillary means further includes, in said intake end, a capillary entrance extending from the exterior surface of the device to one end of said core.

12. A device as defined in claim 11 wherein said capillary passageway has a flow-through aperture, and the maximum dimension of said aperture of said passageway at the point of initiation of said core, and the maximum dimension transverse to flow through said capillary entrance, form a ratio no greater than about 2.5 to 1.

13. A device as defined in claim 11 wherein the flow divergence direction of said capillary passageway at said core initiation point forms a diverging cone angle with respect to the direction of flow of liquid through said capillary entrance which is less than about 45°.

14. A device as defined in claim 13 wherein said core is symmetrical about a center axis and includes a plurality of generally linear, capillary tubes, the midpoints of the entrance of the tubes being aligned along a radius extending outwardly from said axis to form a cone having a diverging cone angle equal to or less than about 45°.

15. A device as defined in claim 11 wherein said capillary entrance has a maximum dimension transverse to fluid flow therethrough no greater than about 0.12 cm.

16. A vented liquid collecting and dispensing device for collecting non-pressurized liquids, comprising a collection compartment having an intake end, a discharge end generally opposite to said intake end, wall means connecting said ends and defining with said ends the interior of said compartment, and capillary means in said compartment for drawing non-pressurized liquid into said compartment at said intake end by capillary attraction, said capillary means subdividing said interior into at least one capillary passageway through which the liquid is drawn by capillary attraction, a dispensing chamber adjacent and in fluid communication with said discharge end and including generally cylindrical walls, a dispensing aperture, and blocking means for temporarily blocking flow of liquid to said dispensing aperture, said blocking means including a rotary valve having a curvilinear valve stem and being disposed for rotation about said aperture, said chamber further including a partition spaced away from said cylindrical walls by a distance which is sufficiently large as to permit passage of said stem and which is sufficiently small as to create a blocking meniscus effect in blood serum which attempts to flow between the cylindrical wall and the partition, a vent passageway extending from an inlet end adjacent to and in fluid communication with said discharge end to an outlet end on the exterior surface of the device, to exhaust air from said compartment as liquid is drawn in, and means for displacing liquid from said capillary passageway into said dispensing chamber.

17. A liquid collecting and dispensing device for collecting non-pressurized liquids, comprising a collection compartment having an intake end and a discharge end generally opposite to said intake end, a dispensing chamber adjacent said discharge end and comprising a cylindrical wall, a valve constructed and mounted for rotation within said walls between a first position for closing said discharge end and a second position for opening said discharge end, and a partition in said chamber spaced away from said cylindrical wall by a distance which is sufficiently large as to permit passage therebetween of at least one portion of the valve and which is sufficiently small as to create a blocking meniscus effect in the liquid introduced at the space between the cylindrical wall and the partition, and means for displacing liquid from said compartment into said dispensing chamber.

18. The device as defined in claim 17 wherein said compartment includes at least one capillary passageway extending the entire sample collection length of the compartment from said intake end.

19. The device as defined in claim 17, and further including a vent passageway extending from an inlet end adjacent to said discharge end to an outlet end on the exterior surface of the device.

20. A collection device for non-pressurized liquids, comprising a collection compartment having an intake end, a discharge end generally opposite to said intake end, wall means connecting said ends to define with said ends the interior of said compartment, and capillary means in said compartment for drawing non-pressurized liquid into said compartment at said intake end by capillary attraction, said capillary means including a core contained within said compartment which creates a path along the compartment for capillary flow of liquid, said path having a cross-sectional area that is less than that of said compartment but greater than the area obtained by multiplying the maximum compartment dimension between said wall means by the maximum depth of sustainable capillary flow, and means for exhausting air from said passageway as liquid is collected therein.

21. A device as defined in claim 20, and further including a capillary entrance extending within the device from said intake end to one end of said core.

22. A device as defined in claim 21 wherein said path has a flow-through aperture, and the maximum dimension of said flow-through aperture at the point of initiation of said core, and the maximum dimension transverse to flow through said capillary entrance, form a ratio no greater than about 2.5 to 1.

23. A device as defined in claim 21 wherein the flow divergence direction of said path forms a diverging cone angle with respect to the direction of flow of liquid through said capillary entrance which is less than about 45°.

24. A device as defined in claim 21 wherein said core is generally conical in shape.

* * * * *

UNITED STATES PATENT AND TRADEMARK OFFICE
CERTIFICATE OF CORRECTION

PATENT NO. : 4,136,036
DATED : January 23, 1979
INVENTOR(S) : Richard L. Columbus It is certified that error appears in the above-identified patent and that said Letters Patent are hereby corrected as shown below:

Column 15, line 54 (claim 5), "chamber is response" should read --chamber in response--.

Signed and Sealed this

Fifth Day of June 1979

[SEAL]

Attest:

RUTH C. MASON
Attesting Officer

DONALD W. BANNER
Commissioner of Patents and Trademarks